United States Patent
von Schrader

[11] Patent Number: 5,598,835
[45] Date of Patent: Feb. 4, 1997

[54] INHALER DEVICE

[76] Inventor: Barthold von Schrader, Ziegelhorst 12, D-23570, Travemünde, Germany

[21] Appl. No.: 284,599
[22] PCT Filed: Nov. 20, 1992
[86] PCT No.: PCT/EP92/02679
   § 371 Date: Aug. 12, 1994
   § 102(e) Date: Aug. 12, 1994
[87] PCT Pub. No.: WO93/15783
   PCT Pub. Date: Aug. 19, 1993

[30] Foreign Application Priority Data

Feb. 13, 1992 [DE] Germany .............................. 9201793 U
Jul. 7, 1992 [DE] Germany .............................. 9209050 U

[51] Int. Cl.$^6$ .......................... A61M 15/02; A61M 11/00
[52] U.S. Cl. ................... 128/200.21; 128/200.14; 128/203.12; 128/203.26; 128/204.13; 128/204.14
[58] Field of Search ........................ 128/200.14, 200.18, 128/200.21, 200.23, 203.12, 203.15, 203.18, 203.19, 203.21, 203.22, 203.23, 203.24, 203.29, 204.13, 204.14; 239/338, 370

[56] References Cited

U.S. PATENT DOCUMENTS

| | | | |
|---|---|---|---|
| 2,445,653 | 7/1948 | White | 128/200.14 |
| 2,586,502 | 2/1952 | Backus | 128/200.21 |
| 2,705,007 | 3/1955 | Gerber | 128/203.21 |
| 4,635,630 | 1/1987 | Noir et al. | 128/203.26 |

FOREIGN PATENT DOCUMENTS

1676631 9/1991 U.S.S.R. .......................... 128/203.12

*Primary Examiner*—V. Millin
*Assistant Examiner*—V. Srivastava
*Attorney, Agent, or Firm*—Salter & Michaelson

[57] ABSTRACT

An inhaler device has a vessel containing the substance to be inhaled and a lid helping to vaporize the substance to be inhaled. The lid includes a generally central opening and several openings positioned in a ring around the central opening. The central opening is formed such that it extends deeper in the vessel than the several openings that are arranged in a ring. The cross-sectional area of the central opening are generally equal to the sum of the cross-sectional areas of the several openings for enabling a sufficient quantity air to be drawn into the several openings to vaporize the substance to be inhaled.

7 Claims, 8 Drawing Sheets

INHALER DEVICE

The invention relates to an inhaler device with a vessel containing the substance to be inhaled and with a lid that helps to vaporize and distribute the substance to be inhaled.

Such inhaler devices are in general filled with a very hot liquid in which the desired substance to be inhaled is dissolved. A vapour containing the substance to be inhaled reaches the air passages through special nozzles for mouth or nose breathing. These known devices call for special care on account of the hot liquid.

It is also known to rub the substance to be inhaled into the skin, e.g. the chest area, and to allow it to vaporize due to the body heat. This intrinsically advantageous method occasionally irritates the skin and is therefore not tolerated in many cases.

The object of the invention is to supply the substance to be inhaled to the air passages directly or via the respiratory air in acceptable form without the use of hot liquids and without rubbing into the Skin. This object is achieved according to the invention by means of an inhaler device with a vessel containing the substance to be inhaled and with a lid that helps to vaporize the substance to be inhaled, which is provided with a substantially central opening and several openings arranged substantially in a ring around the central opening.

Developments of the invention are defined in the subclaims.

In a preferred embodiment of the invention the lid with the two opening systems is adapted to the opening region of commercially available vessels filled with the desired substances to be inhaled (for example available under the trade name WICK VAPORUB) and is screwed down or placed on these then opened vessels. During the operation of such an inhaler device consisting of vessel and lid the substance to be inhaled can be vaporized by the flowing respiratory air or an arbitrary, adjustable air flow and be passed into the air passages. In such an application the central opening is connected to the patient via a breathing tube with mouth piece or nose piece. During sucking in of the respiratory air the external air is then drawn in via the openings arranged in a ring around the central opening in the lid, spreads over the surface of the substance to be inhaled in the vessel and reaches the patient as respiratory air together with the vaporized parts of the substance to be inhaled. Conversely substance to be inhaled vaporized during the expiration is distributed via the ring-shaped openings in the air region around the patient and breathed in immediately or subsequently. In the case of a combination of the inhaler device according to the invention with a commercially available breathing valve, e.g. the breathing valve AMBU of the firm Heraeus, the central opening of the lid is connected to the inlet of the breathing valve and the exhaled air exhaled directly via the valve.

The action of such an inhaler device has proved to be beneficial if the cross-section of the central opening is substantially equal to the sum of the cross-sections of the openings arranged in a ring.

The device can also be employed for enriching the ambient air, by using instead of the respiratory air a fan, such as for example a hair dryer or a fan specially adapted to this application. Preferably such a fan is operated at low temperatures of 50°, because according to further findings temperatures of around or slightly more than the body temperature are beneficial and sufficient for the vaporizing of the substance to be inhaled. Such a device is also advantageous in terms of the energy requirement.

In another embodiment the beneficial vaporizing temperature lying above the body temperature is produced or maintained over a longer time, [so] that the required amount of substance to be inhaled [is] passed into a twin-walled vessel. There can also be introduced into the vessel, separately from the substance to be inhaled, a material which alters its state slightly above the body temperature, for example changes from the liquid into the solid state, and in so doing emits the amount of heat required to maintain the temperature inside the vessel. Such a material is e.g. the material known under the name tetradecanol. It can be introduced into the twin-walled bottom or, loaded into a cartridge, into the vessel.

As a detailed explanation of the invention, several embodiments will be described below with reference to the drawings. These show in FIG. 1 a section through the lid and the vessel of an inhaler device according to the invention, FIG. 2 an overhead view of FIG. 1, FIG. 3a and FIG. 3b an adjustable sealing washer for the lid according to FIG. 1, FIG. 4 a lid according to FIG. 1 without the inserted, adjustable sealing washer according to FIG. 3a or FIG. 3b, FIG. 5a and FIG. 5b a device with breathing mask and breathing tube, FIG. 6 a device with fan, FIG. 7a, FIG. 7b and FIG. 7c a development of FIG. 6 in various views, FIG. 8 a development with a twin-walled vessel, FIG. 9a, b and c a valve interior for the lid arrangement.

Figure 1:
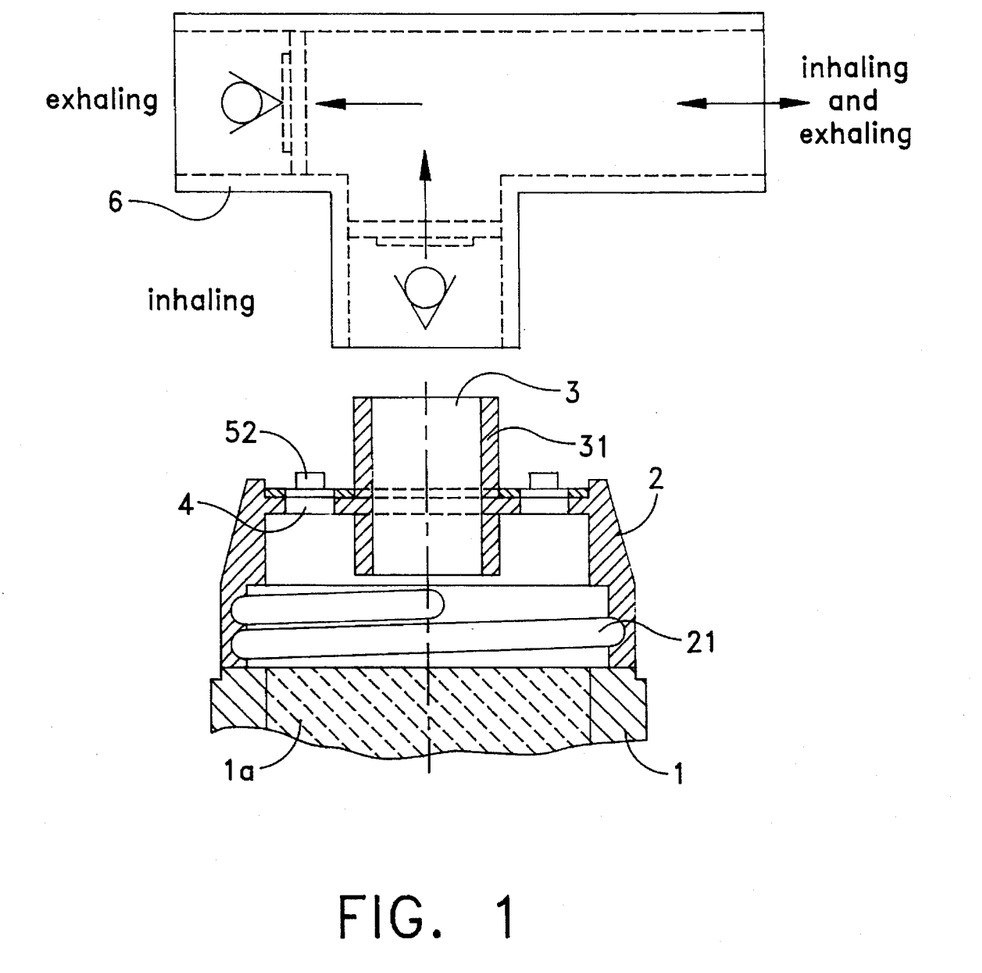

FIG. 1 shows a vessel 1 which is filled with a preferably ointment-like substance to be inhaled 1a. Such vessels are commercially available. There is screwed onto the vessel a lid 2. This lid 2 can already be present as a seal on delivery of the vessel. In this case the vessel 1 is tightly sealed, for example by a heat-sealing film (not shown), which is removed prior to start-up. The lid 2 can also be supplied or used as replacement for the sealing lid originally provided. The lid 2 is provided with a substantially centrally arranged opening 3, which is surrounded by several openings 4 in a ring. The central opening 3 is formed by a tube 31 penetrating the disc-shaped lid surface. The possibility is thus created of the opening 3 being brought to a position close to the surface of the inhaler device. The tube 31 can be fixed, but can also be provided adjustable by lengthwise displacement in order to set the distance from the surface. The lid 2 can, as shown, be connected by means of a screw thread 21 to the vessel 1, which is provided with a similar thread. It can also be pluggable however. In this case it is advantageous to provide a lock-in position.

In the simplest case the tube 31 is provided with or connectable to mouth and nose adapters. In such a form of use the user holds the vessel 1 in the hand and inhales the substance to be inhaled directly through one of the adapters. The vaporizing of the substance to be inhaled is promoted by the hand heat passing onto the vessel 1. This form of use is particularly advantageous for travel purposes.

The central opening 3 can be connected or connectable to a separate breathing valve 6 or a breathing mask. Such breathing valves 6 are for example supplied by the form Heraeus under the trade name AMBU. The tube 31 of the lid 2 is so formed that the breathing valve 6 is pluggable or screwable onto the tube 31. Such a breathing valve permits, if it is combined with the vessel 1 via the lid 2, the easy inhalation of the substance to be inhaled vaporized by means of the openings 4 and an unhindered, easy exhalation through the valve segment of the breathing valve 6.

Figure 2:
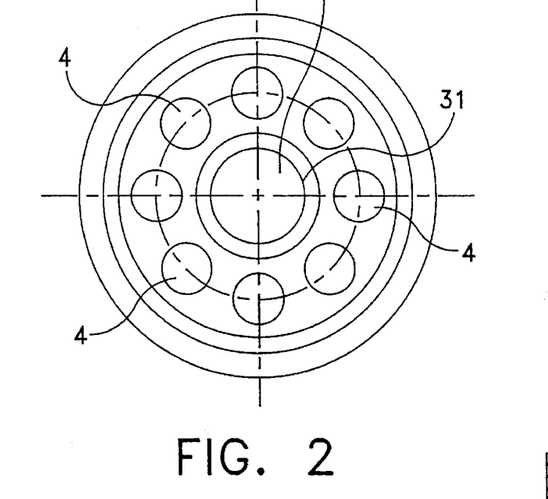

FIG. 2 shows an overhead view of the lid 2 represented in FIG. 1. The openings 4 arranged in a ring around the central opening 3 are arranged in groups. An arrangement of four groups each with 4 holes is shown. Such an arrangement permits a swirling of the flowing air across the surface of the substance to be inhaled or even an adjustable metering. This takes place either by proportioning of the size of the holes 4 or by means of the additional disc 5 shown in FIG. 1, which is insertable into the outside of the lid 2. The mounting of the disc 5 in the lid 2 is so determined that the disc 5 is pivotable in the lid 2 and thus makes the openings 4 sealable. The disc 5 is provided with projections 52 and with holes 41 which match the holes 4 in the lid 2. The disc 5 can be rotatable in positions in which the openings 41 lie above the openings 4 and hence allow free passage. In other positions of the disc 5 the openings 4 are wholly or partly covered by the walls of the disc 5, whereby the resulting opening is reduced or even closed. Intermediate positions therefore produce the required sizes of each of the resulting passage openings. The openings 4 coverable by the disc 5 can also differ in number and size from the openings 41 in the disc 5. For example there can be provided at the position of the projections 52 of the disc 5 an opening 4. The lid 2 can also itself be constructed as a valve and act on the user via a valve-free breathing mask. In this case, on inhalation of the air contained in the vessel 1 and enriched with the substance to be inhaled, the path to the patient is cleared, whereas this path is blocked again on exhalation. Instead a further valve arranged in the lid, which leads to the free air space, is opened.

Figure 3A:
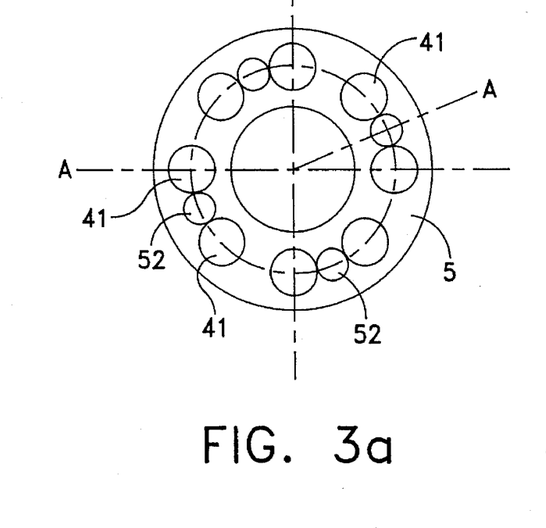
Figure 3B:
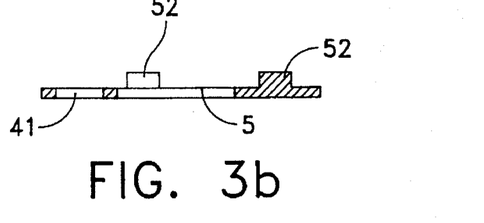

FIG. 3a shows a disc 5 which is provided with openings 41 divided into four groups of two each. There is arranged between each group of two openings 41 a projection 52 which can serve as a handle for the rotation of the disc 5 inserted into the lid 2. FIG. 3b shows the disc 5 in cut-away sectional view. By selection of the section along the lines AA a projection is cut away and a further projection 52 in non-cut-away side view is visible.

The lid 2 can also be laid out for other vessels. It is also possible to provide adapters for connecting such a uniform lid to other vessels. If it used for a vessel which is intended for the dissolving of substances to be inhaled in hot water, there should be provided above a greater vaporizing surface an adapter tapering spherically upwards to the lid 2.

Figure 4:
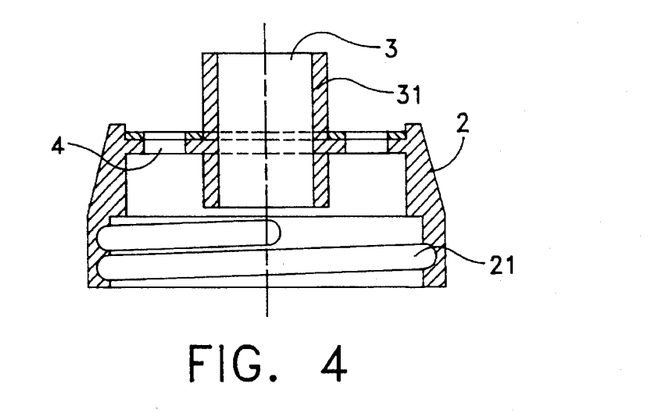

FIG. 4 shows a lid 2 which exhibits the openings 3 and 4 and where the disc 5 has not yet been inserted.

Figure 5A:
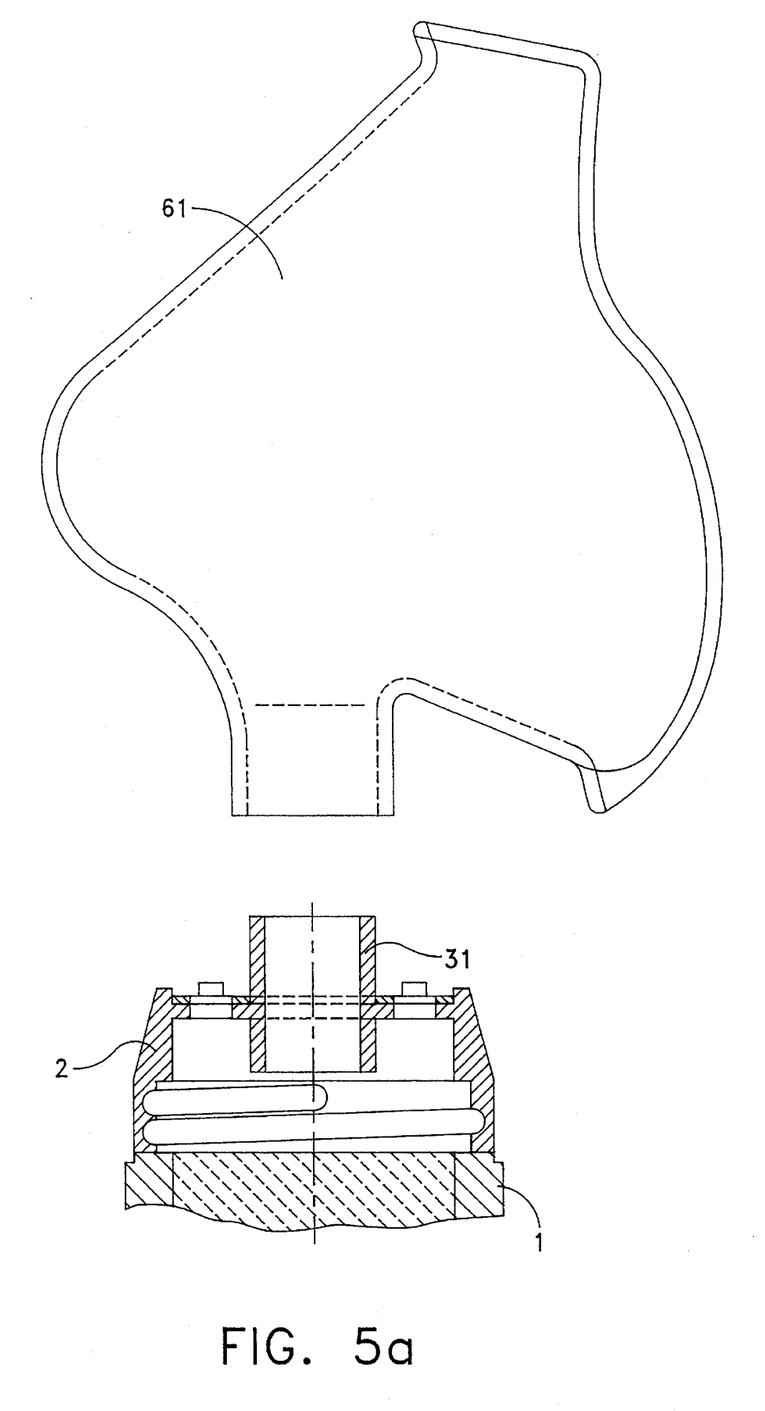

FIG. 5a shows a device with lid 2 and breathing mask 61, which is connectable to the adapter 31.

Figure 5B:
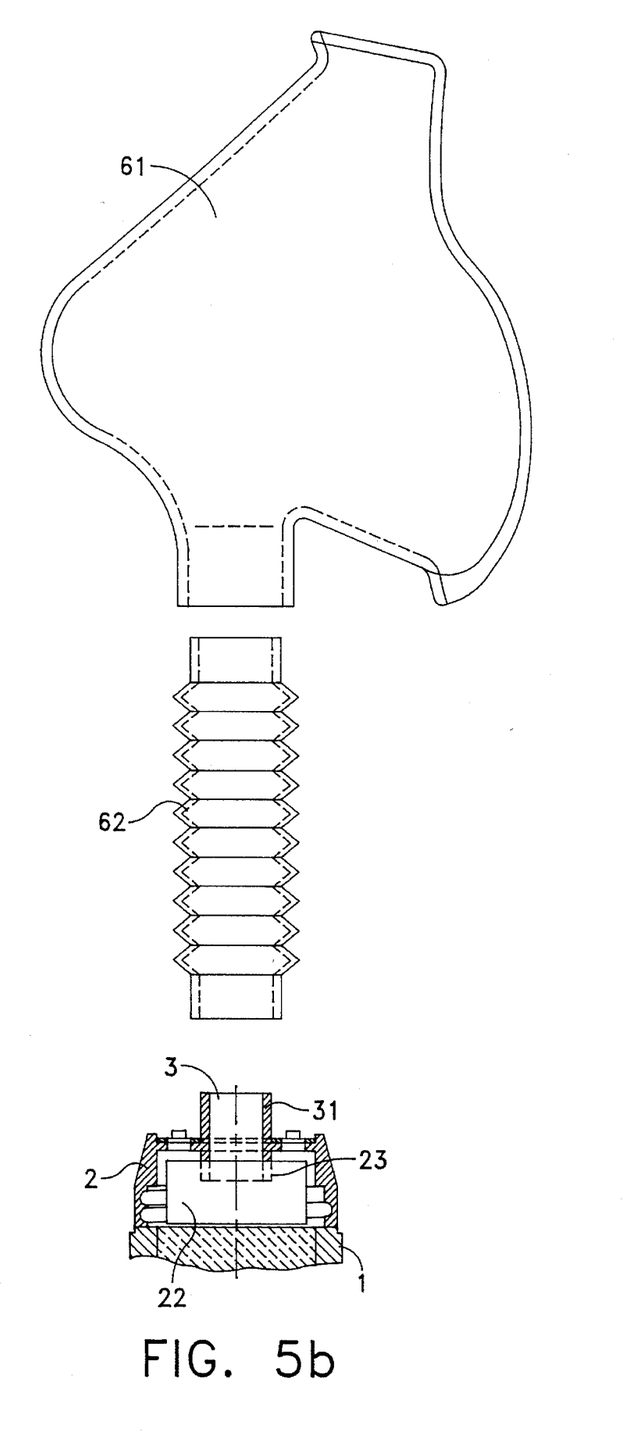

FIG. 5b shows a device with lid 2, breathing mask 61 and with a tube 62 which is shaped for connecting the breathing mask 61 to the adapter 3.

An optimal vaporizing effect is achieved with the lid 2 shown in FIGS. 1–5 if the surface area of the ointment-like material in the vessel 1 is as great as possible. In order to increase this surface area, the amount of material required for one inhalation period can—as shown in FIG. 5b—be deposited on a carrier 22 and the latter be introduced into the lid 2 or the filled or empty vessel 1.

The lid 2 can be provided with a receiver 23 for the carrier 22, so that the surface is particularly exposed to the breath flow. The carrier 22 can be a moulding, but can also be formed from shapeable paper or similar and be inserted into the receiver 23, e.g. into a slot in the pipe 31. The particular amount of material required can be obtained from a back-up vessel.

Figure 6:
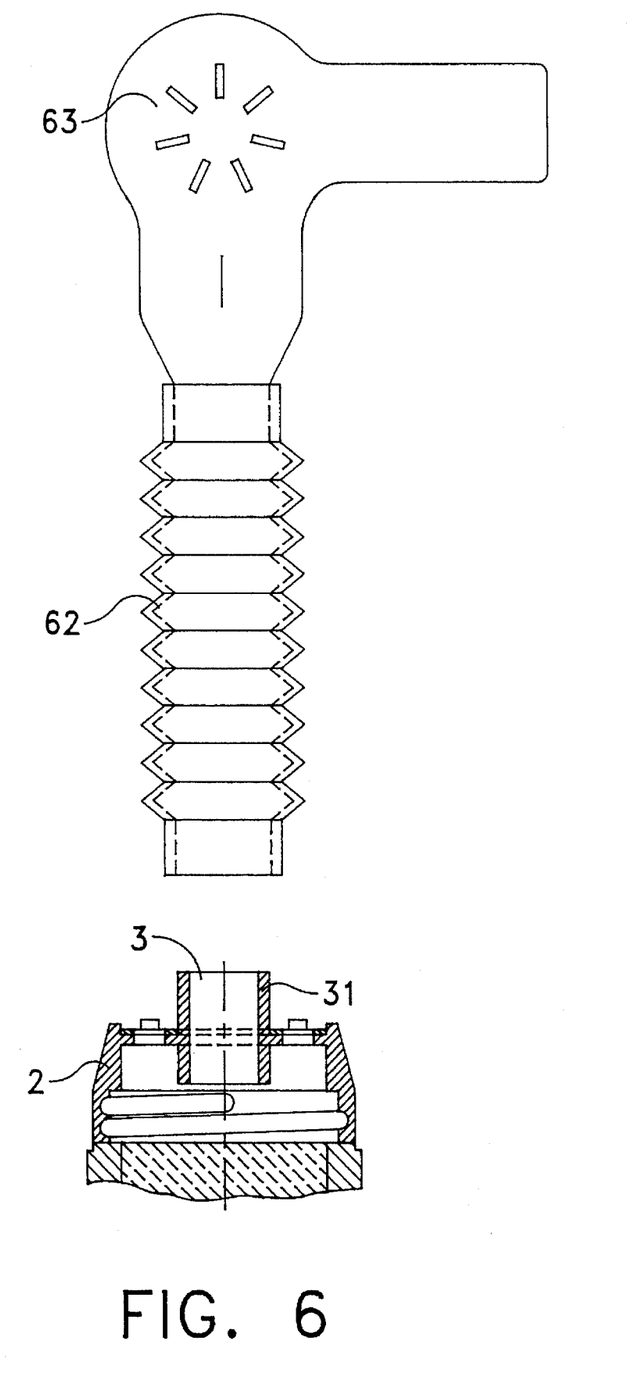

FIG. 6 shows the use of the device for the enrichment of the respiratory air with the inhalation particles. To this end the adapter 3 is connected directly or via the breathing tube 62 to a fan 63, e.g. a commercially available hair dryer or similar. Since such hair dryers are specially available also for travel purposes and form part of the room fittings in many hotels, a person can also carry out direct or indirect inhaling with the device described when travelling. Commercially available hair dryers or fans can be provided with a standardized opening for the connection of the device. If such a standardized opening is not available, the shape of the breathing tube can be suitably varied to make it connectable to various openings. This can be done either by means of an expandable connection or by a range of connections.

FIG. 7a shows an inhaler device with vessel 1 and lid 2, which are combined into a compact unit together with a heater fan 63. The lid 2 is provided on its outer wall 24 with a stop 25, which is formed in a ring shape, but can also exhibit only individual projections. The lid 2 is connected to a casing 64 of the fan 63. This casing 64 contains on the one hand the fan motor 65 and on the other an air duct 66 with a heater 67 in the flow path of the air. The casing 64 is provided at the end of the flow path 66 on the side facing the lid 2, in FIG. 7a on its bottom side, with an opening 68 adapted to the lid 2, which is bounded by the outer wall 24 of the lid 2. The length of the tube 31 of the lid 2 and the dimensions of the casing 64 are so proportioned that the tube 31 penetrates the wall of the casing 64 through an opening 69 on the side of the casing 64 which lies opposite the opening 68.

When the fan 63 is switched on, the air drawn in by the motor 65 flows through the heater 67 into the air duct 66 of the casing 64 and through the opening 4 in the lid 2 into the vessel 1, mixes there with the vaporized particles to be inhaled and passes through the tube 31 to the breathing mask 61 or into the open environment.

The vessel 1 is lockable. It is also possible to restrict the flow path for the air and/or the sir-particle mixture. In both cases motor 65 and heater 67 can cause excessively high temperatures. In order to prevent damage to the fan 63 by overheating of the casing 64 and/or of the motor 65, motor 65 and heater 67 can be switched off or regulated down automatically in the event of air build-up or overheating.

FIG. 7 shows a device in which instead of such an automatic switching off the casing 64 itself is so constructed that in each case a minimum air flow is maintained for the fan 63 and overheating is therefore avoided. To this end the opening 69 in the casing 64 is proportioned slightly more generously than the outer wall of the tube 31 penetrating the casing 64, so that the air flow generated by the fan 63 can escape with a minimum component through an additional opening 691 parallel to the tube 31 out of the casing 64. This additional opening 691 can in the case of combined unit 2, 64 be so proportioned or shaped that the air flow escaping from the opening 691 intermingles with the inhalation-air-particle mixture escaping from the tube 31. Since the air escaping in this way is warmer than the air-particle mixture escaping from the tube 31, the respiratory air can be preheated artificially. The additional opening 691 can also be formed or amplified by a plurality of nozzles arranged obliquely to the tube 31 for the intermingling of air and particles.

Figure 7B:
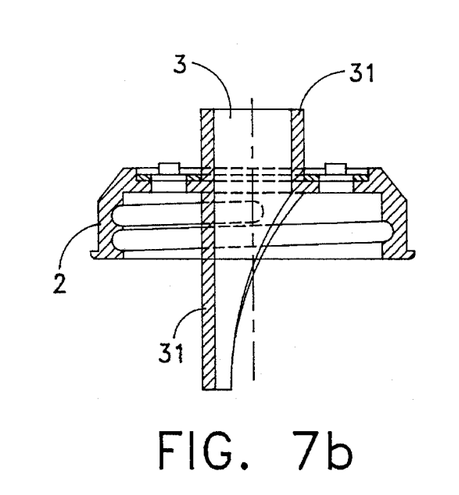
Figure 7C:
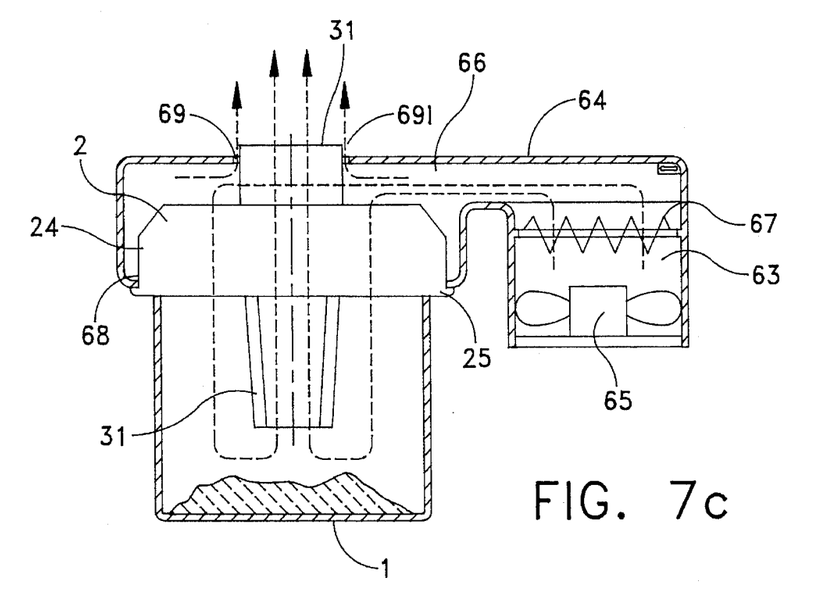

FIG. 7b shows a section through the lid 2 represented in FIG. 7a. The tube 31 is provided on its side projecting into the vessel 1 with an obliquely cut opening 32. The vaporizing in the vessel is promoted by this layout. FIG. 7c shows a side view of FIG. 7b with the visible cut-away edges of the tube 31. The vaporizing can be promoted still further if prior 
to use there are placed in the vessel 1 porous clay bricks or similar. The latter can also be preheated.

Lid 2 and casing 64 are in FIG. 7a two separate, joinable parts. The lid 2 can however also be manufactured in a single piece with the casing 64 and thus form with the latter one structural unit, into which the vessel 1 is screwed. Motor 65 and heater 67 can be operated with mains voltage. Because of the relatively low temperatures and the consequently low heating output it is also possible to run such inhaler devices from batteries, e.g. in a car. The connection for cigarette lighters provided in cars is for example suitable for this purpose.

With the device shown in FIG. 7a it is possible to enrich the respiratory air of bed-ridden patients in rooms or areas of rooms with the aromatics of the ointment-like or liquid medicines prepared or suitable for this purpose.

Figure 8:
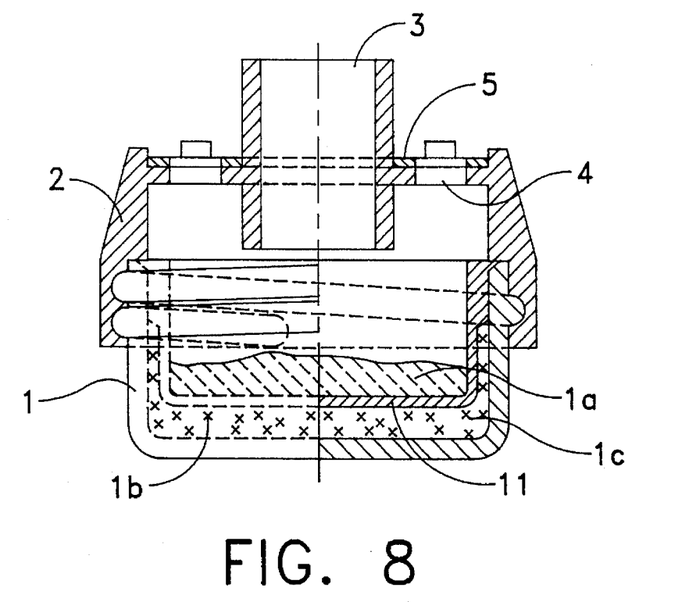

FIG. 8 shows a vessel 1 with lid 2 as per FIG. 1, with which an overall vessel 1, 11 with twin walls is obtained by means of an insert 11. On the one hand the temperature of the substance to be inhaled 1a is kept in the optimum vaporizing range for a protracted period simply by means of these twin walls 1, 11. On the other hand these twin walls permit the use of an agent 1b for stabilizing the heat which is separate from the substance to be inhaled 1a. There is provided as heat stabilizing agent 1b a material which can absorb and store heat and which is capable of emitting this heat again over a protracted period. Such a material is for example clinker brick meal, which is heated separately and then loaded into the vessel cavity 1c between the walls 1 and 11. Preferably however a material such as tetradecanol is used, which is loaded already during the manufacture of the vessel 1, 11 into the cavity 1c and remains there. This material has the advantage that it passes just above the body temperature from the liquid state into the solid state and during this passage in the range of about 38° maintains or emits heat of this temperature over a protracted period.

If the vessel 1, 11 together with the temperature-sensitive material 1b contained in the cavity 3c is washed or heated for sterilization at 100°, the temperature-sensitive material 1b is liquefied at the same time. The substance to be inhaled 1a is then loaded and the lid 2 screwed on. The temperature of the vessel 1, 11 together with contents 1a and 1b will drop until the temperature-sensitive material 1b passes into the solid state in the range of about 38°. In this range the temperature of 38° is then held for a protracted period. The vessel 1 does not however always have to be heated to 100° in order to achieve the temperature profile described. Heating to only about 50° brings about liquefaction of the material and the described heat retention and heat emission with renewed passage into the solid state.

The heat-stabilizing action of the tetradecanol is also exploitable with simply constructed vessels according to FIG. 1. In such cases this material is loaded into cartridges or similar, which are then placed in the vessel 1 filled with material to be inhaled 1a.

Figure 9A:
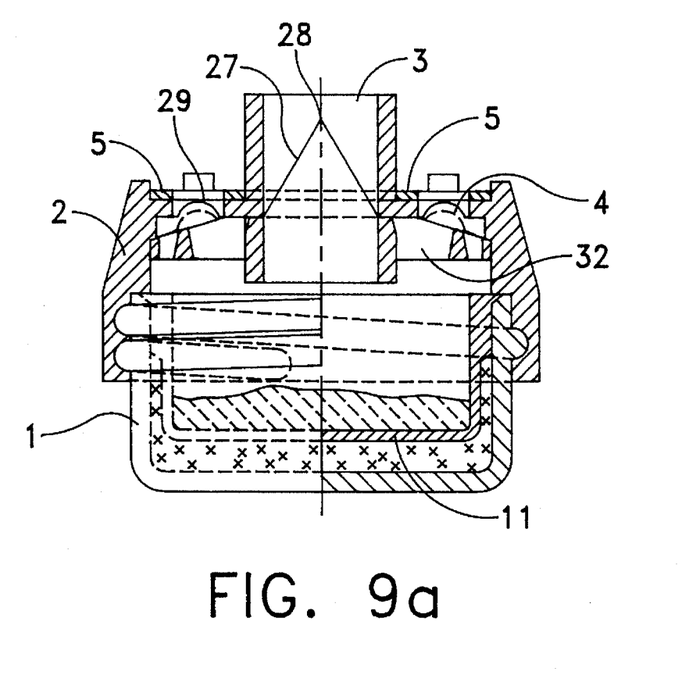
Figure 9B:
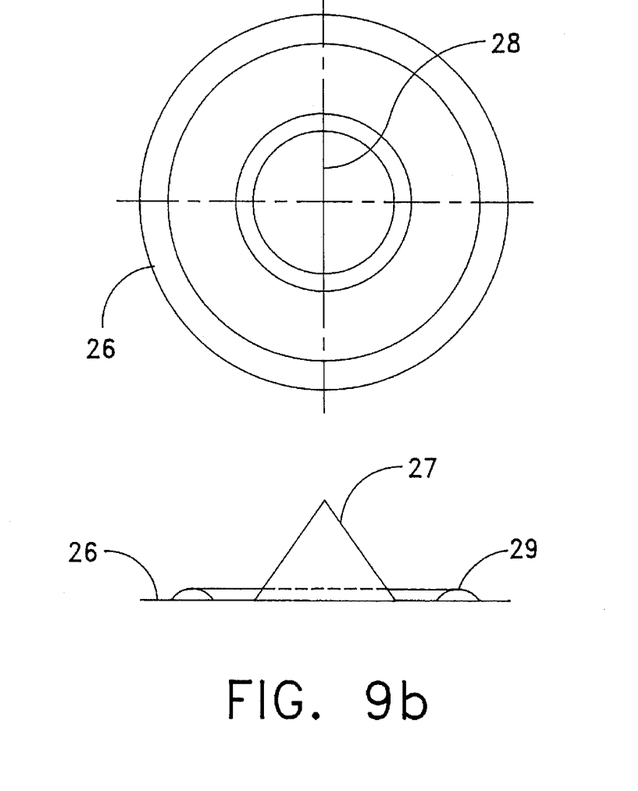
Figure 9C:
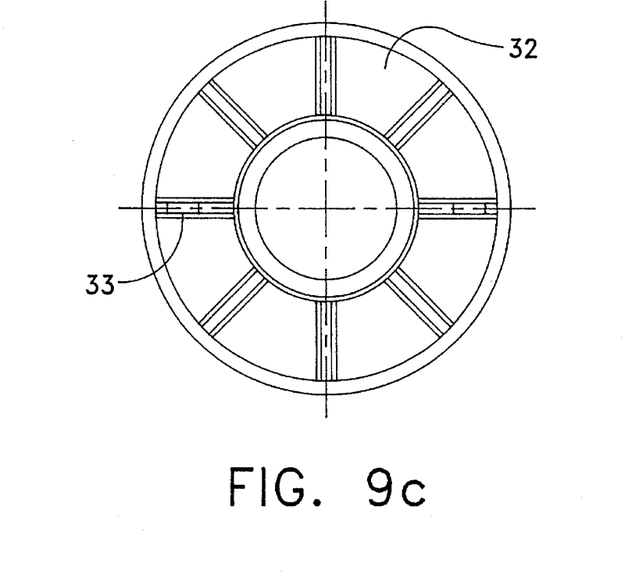

In the case of applications with only small metering rates it may happen that the steady heat produces excessively high evaporation losses, if breathing valve devices., e.g. according to FIG. 1, are not used. FIG. 9 shows a lid arrangement for avoiding or reducing evaporation losses. On the inside of the lid 2 a combined membrane and lip seal 26, 27, 28, 29 is provided. This combined seal locks the vessel 1 so long as no inhalation via it takes place. During exhalation and also during temporary non-use the vessel 1 is locked for practical purposes. To this end a one-part membrane 26 with a cone 27 projecting into the central opening 3 of the lid 2 is provided, which cone 27 is provided with a slot 28 forming the lip seal. In the region of the openings 4 of the lid 3 the membrane 26 is moulded with bosses 29, which lock the openings 3 in the idle position. On the side of the membrane 26 facing away from the lid 2 there is arranged and connected firmly to the lid 2 a stabilizing grating 52, which holds and supports the membrane 26 and optionally additionally with springs 33 presses the bosses 29 against the openings 4 in order to reliably lock the latter.

FIG. 9*b* shows the membrane 26 in overhead view in order to make clear the slot 28. FIG. 9*c* shows in overhead view the stabilizing grating 32.

On inhalation of the air through the opening 3 the membrane 26 bends at its edge region downwards and allows air to flow across the heated material to be inhaled 1*a*. At the same time this air is swirled through the openings 4, the bosses 29 and the bent down edge region of the membrane and passes with entrainment of traces of the material to be inhaled 1*a* through the slot 28 in the cone 27 of the membrane 26 through the opening 3 to the inhaling person. Since the air penetrating into the vessel 1 from the outside of the membrane 26 passes along the heated walls of the vessel 1, it is already heated before reaching the material to be inhaled. The swirling of the heated air with the traces or particles of the material to be inhaled 1*a* promotes the good effect of the inhalation.

The membrane device can be employed together with the control disc 5, but can also be used without this control disc 5.

I claim:

1. Inhaler device with a vessel (1) containing the substance to be inhaled and with a lid (2) helping to vaporize the substance to be inhaled, which is provided with a generally central opening (3) and several openings (4) positioned in a ring around the central opening (3), said central opening (3) extending deeper in the vessel (1) than the several openings (4), the cross-sectional area of the central opening being generally equal to the sum of the cross-sectional areas of the several openings for enabling a sufficient quantity air to be drawn into the several openings to vaporize the substance to be inhaled.

2. Inhaler device according to claim 1, further comprising a disc (5), the lid (2) being locked on its outside by said disc (5) for sealing the vessel contents evaporation-tight.

3. Inhaler device according to claim 2, said disc (5) being rotatable relative to the lid (2) and comprising holes (41) which form an air passage in the lid (2) with the several openings (4).

4. Inhaler device according to claim 3, a ring-shaped groove (8) being provided for the mounting of the disc (5) in the lid (2).

5. Inhaler device according to claim 1, the opening being formed by a tube (31) which is shaped for connection to mouth and nose pieces, for breathing masks.

6. Inhaler device according to claim 5, said tube (31) having a valve sealing the tube, which offers a slight resistance to the inhalation of the patient.

7. An inhaler device comprising a vessel that contains a substance to be inhaled, and a lid for vaporizing the substance to be inhaled, said lid being provided with a generally central opening and several circumferential openings positioned generally in a ring around the central opening, said central opening extending deeper in the vessel than the circumferential openings, the cross-section of the central opening being generally equal to the sum of the cross-sections of the circumferential openings.

* * * * *